United States Patent [19]

Barber

[11] Patent Number: 4,558,694

[45] Date of Patent: Dec. 17, 1985

[54] ULNAR DEVIATION SPLINT

[76] Inventor: Lois M. Barber, 728 Ocean Blvd., Pismo Beach, Calif. 93449

[21] Appl. No.: 544,284

[22] Filed: Oct. 21, 1983

[51] Int. Cl.$^4$ ............................................. A61F 5/10
[52] U.S. Cl. ................................................. 128/87 A
[58] Field of Search ................. 128/87 A, 87 R, 77, 128/89 R, 26, 81 R; 273/54 B

[56] References Cited

U.S. PATENT DOCUMENTS

| | | | |
|---|---|---|---|
| 732,532 | 6/1930 | Fallek | 273/54 B |
| 2,595,640 | 5/1952 | Christopoulos | 128/81 R |
| 3,189,025 | 6/1965 | Yaklin | 128/77 |
| 3,497,218 | 2/1970 | Johnston | 273/54 B |
| 3,640,532 | 2/1972 | Bauer | 128/26 |
| 3,703,894 | 11/1972 | Galloway et al. | 128/77 |
| 3,942,522 | 3/1976 | Wilson | 128/89 R |
| 4,456,002 | 6/1984 | Barber et al. | 128/87 A |

OTHER PUBLICATIONS

The Lancet, New Inventions, Feb. 3, 1962, pp. 252 and 253, A Versatile "Lively" Splint.

Primary Examiner—C. Fred Rosenbaum
Assistant Examiner—Christa K. Scott
Attorney, Agent, or Firm—George F. Bethel; Patience K. Bethel

[57] ABSTRACT

A hand splint is provided which is designed to support the metacarpophalangeal joints and resist ulnar drift of the proximal phalanges, while at the same time avoiding restriction of normal hand use. The splint has a bendable support frame of a generally oblong shape which is adapted to fit the palmar arch of the hand. Four generally rounded finger separators are attached to the frame to separate each of the fingers and provide lateral resistance to ulnar drift thereof. Preferably the support frame and finger separators are formed of wire. The entire splint is enclosed in a pliant foamed cushioning material which according to one embodiment can be further covered with an abrasion resistant, flexible outer sheeting material to resist wear. Straps or other fastening means are used to secure the splint against the hand. A process for making the splint is also provided.

19 Claims, 12 Drawing Figures

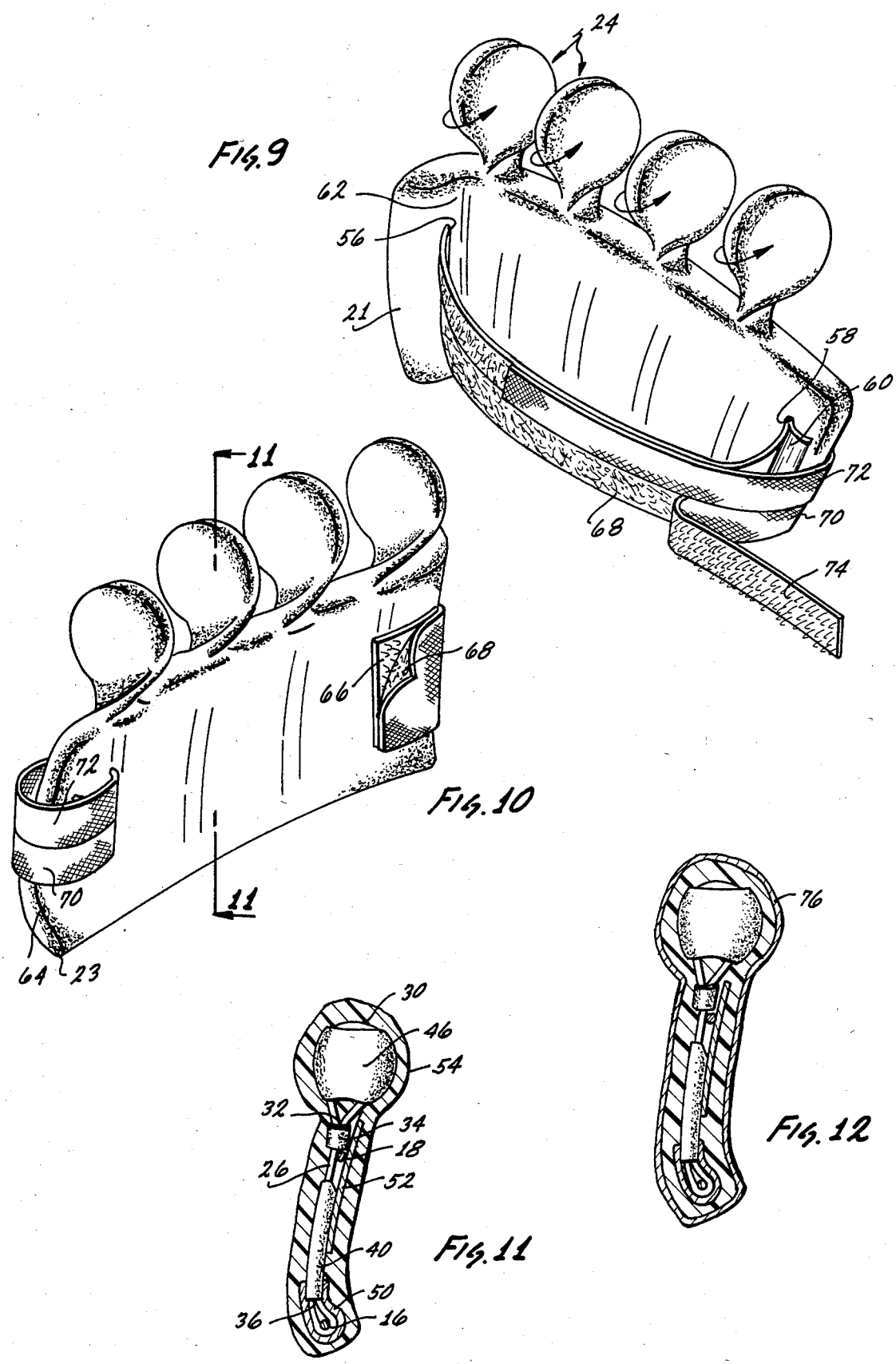

ULNAR DEVIATION SPLINT

BACKGROUND OF THE INVENTION

1. Field of the Invention

This invention relates to the field of hand splints and especially to a hand splint which is particularly designed for arthritic patients to support the metacarpophalangeal joints while at the same time to align the proximal phalanges when indicated by ulnar drift.

2. Description of the Prior Art

In recent years, numerous hand splints have been invented which constituted a major improvement over the wood and plaster splints commonly used in the past. The latter splints, while suitable for certain types of correction and straightening of bones were found to be quite unsuitable for the correction of problems unique to arthritic patients. These patients require more flexible and especially adjustable splints which enable the gradual urging of the bones back into the normal position, as well as adjustments to allow for swelling. Another requirement is to have a splint which can be easily put on and removed by such a patient. Other desirable features include washability, durability and light weight.

Perhaps most important to the patient is a combination of comfort and at least partial use of the hand during wear. Comfort requires soft edges and surfaces to prevent pressure problems. Splint design must allow for the normal palmar arch of the hand. Also, support is desirable for the ulnar side of the hand. The thenar eminence (ball of the thumb) should be kept free to permit movement of the thumb during wearing of the splint.

The newer splints have embodied some of the above characteristics, being usually formed of a combination of wires and rubber bands. Other splints have combined spring wires and other wire frameworks. Tension is often provided by means of rubber bands which are generally looped over angled projections from the device. The implacement of these rubber bands is extremely difficult for arthritic patients and others with hand injuries. Furthermore, the protruding portions of the splint tend to catch on things during the wearing thereof.

Felt is normally used as a cushioning material which does not permit washability or waterproof characteristics. The splint is thus limited in use around water since the felt will become wet and the metal parts subject to attack by moisture.

Furthermore, a flat piece of wire or steel is commonly utilized as the palm piece in prior art hand splints which do not accommodate the normal palmar arch of the hand resulting in a lack of comfort.

In addition, flat wire and steel bands are too rigid and are not capable of custom fit so that there is often a misfit between the splint designed for an average normal hand and the configuration of an injured or arthritic hand.

There are many different types of correction of the hand and fingers required in the treatment of hand injuries and especially of arthritic patients. This has required great ingenuity on the part of occupational therapists and orthopedic doctors to provide just the proper amount of correction while maintaining use of the hand. This has given rise to many specialized splints, each designed to correct and treat a specific injury or condition.

SUMMARY OF THE INVENTION

The ulnar deviation splint of the invention overcomes the deficiencies of the prior art by providing a splint which is light in weight, easily put on and taken off and capable of individual custom fit by virtue of its bendable nature without the need of special tools.

The splint includes a bendable, preferably wire, support frame engagable with the palm of a hand. A plurality of bendable finger separation members are attached to the frame to resist ulnar drift of the fingers. The entire framework is enclosed in cushioning material, preferably a foam plastic.

Fastening means in the preferred form of detachable straps are secured by means of hooked areas in conjunction with interlocking brushed material.

In its most preferred form, the splint includes a framework of wire shaped to a generally oblong shape having two elongated members which are curved to fit and support the palmar arch of the hand. Two shorter connecting pieces unite the elongated members. An end section of the elongated members of the frame is bent upwardly to cup the ulnar side of the hand. Also, an end section of the connecting piece adjacent the radial side of the hand is bent downwardly to fit the curve of the palm at the edge of the thumb. This allows free use of the thumb during the wearing of the splint.

Between the elongated members of the frame are disposed four finger separators in the form of substantially rounded members. These rounded members are preferably attached to the frame by means of a first and second extension. The rounded members separate the fingers during use and provide lateral resistance to ulnar drift or deviation thereof.

The entire splint framework including the finger separators is enclosed in a sandwich of foamed cushioning material, preferably a heat-sealed closed cell polyethylene foam, to provide support and comfort during use. The preferred material, a foamed plastic, is waterproof and washable which further increases its convenience and desirability.

Fastening means for the splint are preferably in the form of washable, detachable straps, preferably incorporating a hooked area in conjunction with an interlocking brushed material. The straps pass over the back of the hand to permit the easy attachment and detachment of the splint. This is especially appreciated by arthritic patients who commonly have limited use of their hands and fingers and find most fasteners difficult to operate.

Another advantage is the use of two straps, one of which extends proximally to the MP (metacarpophalangeal) joint and the other of which extends distally to the MP joint. This distributes the pressure of attachment and at the same time prevents slipping of the splint on the hand.

The splint is customized to fit the right or left hand. The right and left hand splints constitute mirror images of each other. Various sizes of the splint can be made to fit different sized hands. Furthermore, the inner wire framework permits custom fitting of the splint to each hand without special tools. This is also useful to accommodate any changes in the hand due to the correction thereof or to other changes such as swelling.

The exterior cushioning material is soft and washable. Such provision enables showering and other activities around water to be engaged in without damage to the splint.

If additional wear resistance is required either on the palm or back of the splint, an additional layer of abrasion resistant sheeting such as leather or vinyl can be adhered thereto.

In addition to its uses for the arthritic patient, the splint is also efficacious as a PIP (proximal interphalangeal) stop splint to encourage PIP flexion after injury or surgery. It can also be used in the treatment of traumatic injuries, fractures, nerve injuries, burns and other disabilities where ulnar deviation PIP flexion problems need treatment.

A process for making the ulnar deviation splint is also provided. The steps of the process include bending wire to provide a support frame proportioned to fit and contact at least a portion of the palm of a hand to be treated. Further, wire is bent to provide a plurality of finger separator members for resisting ulnar drift of the fingers.

The wire support framework and finger separators are then enclosed at least in part with a cushioning material. This step is followed by attaching fastening means to hold the splint in place against the palm and fingers.

BRIEF DESCRIPTION OF THE DRAWINGS

The invention will be more readily understood by reference to the attached drawings taken in conjunction with the description which follows.

FIG. 9 shows the structure of FIG. 8 which constitutes the dorsum or back of the finished splint;

FIG. 10 shows the palmar side of the splint;

FIG. 11 shows a cross section taken along lines 11—11 of FIG. 10; and,

FIG. 12 shows another embodiment of the invention which includes an outer layer of abrasion resistant material.

DETAILED DESCRIPTION OF THE EMBODIMENTS

Figure 6:
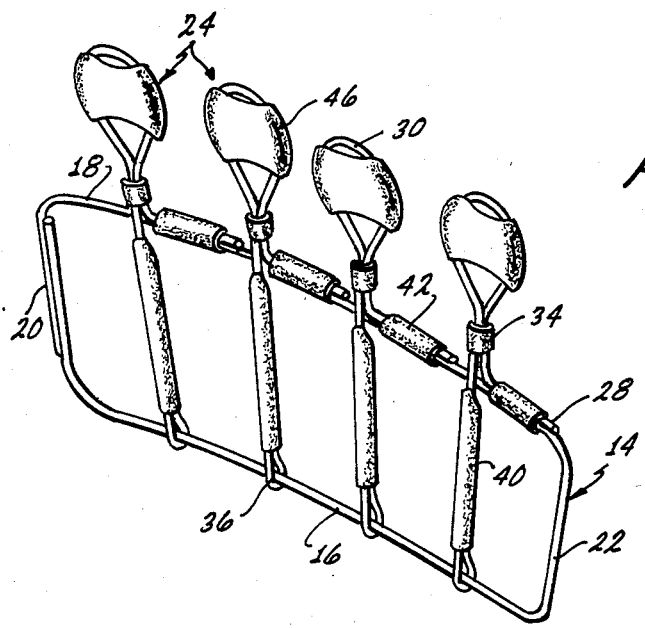
FIG. 6 shows the basic support frame and finger separator members of the splint prior to any bending to fit the contours of the hand.

Referring now to FIG. 6, there is shown a wire support frame 14 which has been bent into a generally oblong shape having two elongated members 16 and 18 of unequal length. The longer, top member 18 is joined to the shorter member 16 by means of an ulnar connecting piece 20 and a radial connecting piece 22.

It can be seen that the support frame 14 is made of a single piece of wire which is joined on the ulnar side 20. Attached to the frame are four individual, substantially flat rounded finger separators 24 which are attached to the support frame 14 by means of extensions 26 and 28 as indicated in FIGS. 4–7.

Each of the finger separators 24 is formed of a piece of wire which is bent into a generally flat rounded member 30 from which extensions 26 and 28 project. The two extensions 26 and 28 diverge from the rounded member 30 at neck 32 which is surrounded by a small section of plastic sleeve 34.

The first leg extension 26 includes a loop 36 at its base through which the bottom frame member 16 is threaded therethrough. The end 38 of the extension 26 is doubled back on itself and held in place by means of a length of surrounding shrink fit plastic tube 40. This serves to add strength to the supporting framework and also to help keep the finger separator 24 on the frame 14.

The second extension 28 of the finger separator 24 is held against the top frame member 18 by means of a section of plastic sleeve 42 as shown in FIG. 6. A further section of shrink fit plastic sleeve or tube as indicated at 44 in FIG. 7, serves to keep each of the finger separators 24 in place and at the desired spacing between them. This spacing is preferably equidistant from each next adjacent finger separator. The outer finger separators are preferably also the same distance from the ends 20 and 22.

In order to provide additional strength to the rounded members 30 of the finger separator 24, they are at least partially covered with a piece of shrink fit plastic tube 46.

Figure 7:
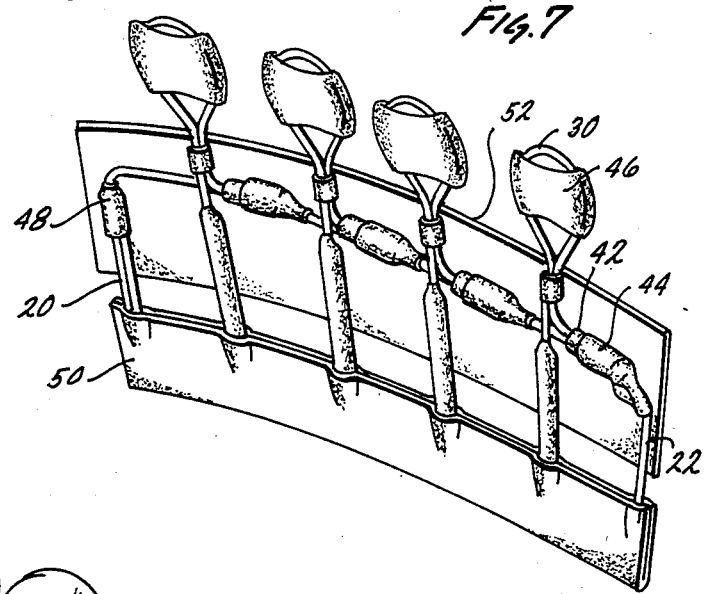
FIG. 7 shows the basic framework of FIG. 6 with the addition of a first layer of cushioning material.

It is also preferred to cover with shrink fit plastic tube any sharp areas or angles 48 of the frame and finger separators as shown in FIG. 7.

In order to stabilize the loops 36 of the finger separators 24 in place on the base 16 of frame 14, it is preferred to enclose them as shown in FIG. 7 with a folded over strip of adhesive backed plastic foam sheeting 50.

Another strip of plastic foam sheeting 52 is adhered to the top frame member 18 of support frame 14 to provide cushioning as well as increased durability.

Figure 8:
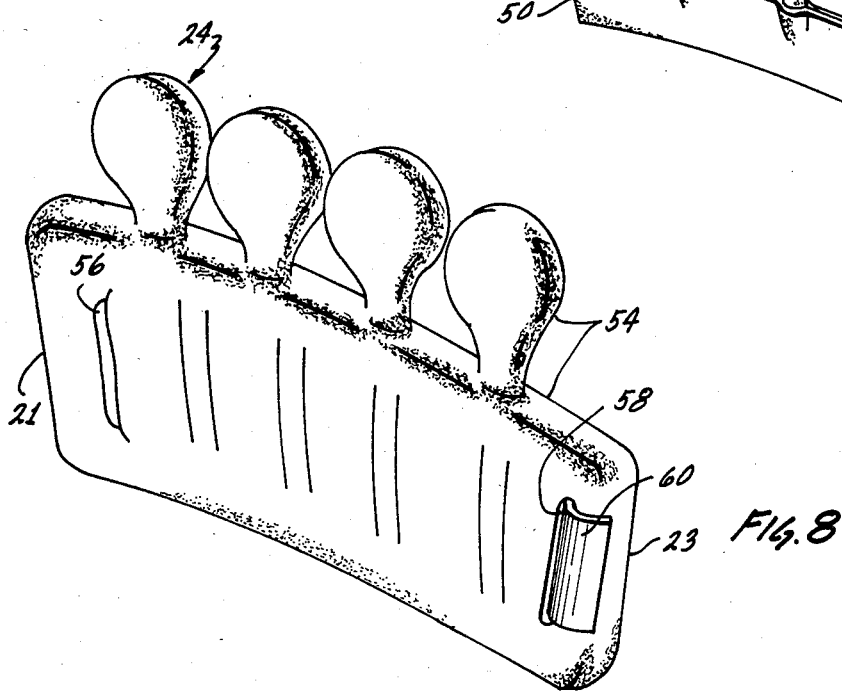
FIG. 8 shows the basic structure of FIG. 7 after enclosure in a sandwich of foam cushion sheeting and slit openings for straps.

Surrounding the frame 14 and finger separators 24 as shown in FIG. 8 is foam plastic sheeting 54. The foam plastic sheeting 54 completely surrounds and seals the splint rendering it waterproof. Normally, the cushioning material 54 is applied prior to bending of the splint to its preferred conformation.

FIG. 8 shows the splint after being enclosed with the cushioning material 54. Also, there is shown a slit opening 56 on the ulnar side 21 of the splint and a slit 58 on the radial side 23 of the splint. A section of slit plastic sleeving 60 is inserted within the slit 58 to partially surround the radial side of the splint. If desired this can be anchored with a small amount of an adhesive.

Figure 3:
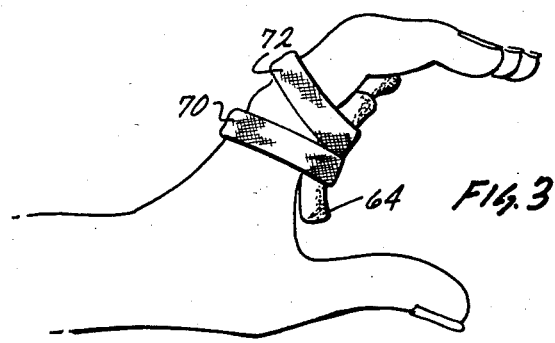
FIG. 3 shows a side view of the hand with the splint in place.

At this point, the splint is bent to its preferred conformation. The first bend is made at the end of the elongated members 16 and 18 on the ulnar side 21 to cup the ulnar side of the hand. This can be seen at 62 in FIG. 9. Also, a portion of the radial connecting piece 22 is bent to fit the curve of the palm at the edge of the thumb. This can be seen at 64 in FIGS. 3 and 10.

Figure 1:
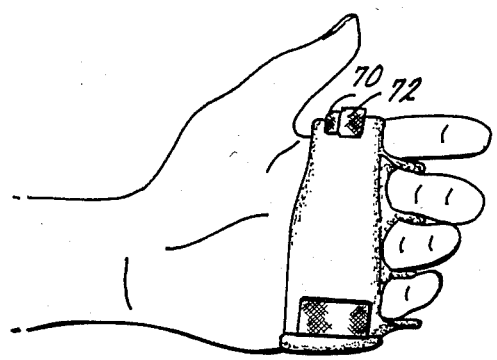
FIG. 1 shows a perspective view of a hand with the under or palmar side of the splint of the invention.
Figure 2:
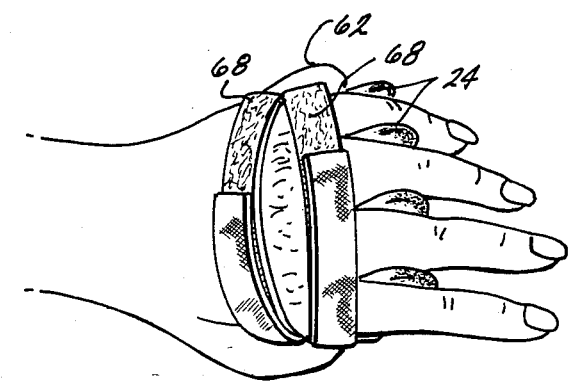
FIG. 2 shows a slightly perspective view of the dorsum or back of the hand with the splint in place.

Next, each of the rounded members 30 of the finger separators 34 is rotated as indicated in FIG. 9 so that each member 30 is at a substantially right angle to the top frame member 18 of the splint. This permits each of the fingers to be separated by the rounded members 30 as shown in FIGS. 1 and 2.

A cross section taken along lines 11—11 of FIG. 10 is shown in FIG. 11 and indicates the turned condition of the finger separator 24.

The splint is provided with detachable straps which are preferably in the form of a laminate of foam between a jersey material and a brushed Nylon material which is interlocking with a hooked area on the straps and a hooked area on a portion of the splint. As shown in FIG. 10, there is a hooked area 66 on the palmar side of the splint. This area 66 interlocks with a brushed Nylon material 68 located at one end of the straps 70 and 72. The straps 70 and 72 extend from this end where they divide into their separate pieces. From the brushed material end 68, the straps pass through slit 56 to the back of the splint where they are threaded downwardly through slit 58 around sleeve 60 and the radial side 23 of the splint. Here, each of the straps 70 and 72 is provided with an area of hooked material 74 located near the ends of each of the respective straps. Since one side of the straps is composed of a brushed Nylon material which interlocks with the hooked area, the straps can easily be adjusted to provide custom fit of the splint and to provide easy adjustment.

While the splint is enclosed in a plastic foam cushioning material, in some instances it might be desirable to have an additional layer of an abrasion resistant material adhered thereto. For example, in the cross section of FIG. 12 there is shown an additional layer of vinyl adhered to the plastic foam cushioning material, as indicated at 76. The addition of the abrasion resistant material, for example vinyl or leather, provides greater wear resistance, especially when the material is on the palm portion of the splint. The extra layer of abrasion resistant material also provides greater durability to the splint.

It is preferred that the frame and finger separators be made of a copper wire. Other types of wire can be used, such as steel, brass, aluminum and the like, but they are not generally available in the strength needed. Excellent results have been obtained using fourteen gauge copper wire for the frame and sixteen gauge copper wire for the finger separator members.

The plastic sleeve material which is used on the neck 34 of the finger separators 24 as well as the sleeves 42 on the top bar 18 of the frame 14 are preferably of plastic made from polytetrafluoroethylene fluorocarbon resins and polyfluorinated ethylene-propylene resins sold under the trademark Teflon, and plastics made from a long chain synthetic polyamide, known generally as Nylon. The important property which is desired is the strength of the materials. Thus, any similar plastic tubing can be substituted therefor.

The shrink fit plastic can be of any type, such as for example, shrink fit polyethylene and ethylene polymer, Teflon, polyolefin, polyvinylchloride, polypropylene and Nylon. The exact choice is not critical. Of the above mentioned shrink fit plastics, the polyolefin has given excellent results. The advantage to the shrink fit tubing is that it holds the various frame pieces together, covers sharp bends and edges and adds strength as well as non-slip characteristics.

The preferred cushioning material is that of a flexible plastic foam, preferably a heat sealable closed cell polyethylene foam. It is preferred for its characteristics of low water absorption, heat sealability, good energy absorption, water vapor barrier, compressiblity, smooth surface, thermal stability up to 215 degrees F., and a high ratio of tensile and shear strength to weight compared to other resilient frames. Polyethylene foam is obtainable in the form of a sheet material. If desired, an adhesive can be applied such as provided by two sided tape adhesives made by 3-M. When the polyethylene foam is used, a sandwich of the material is created with the frame adhered to pieces of foam which are subsequently heat sealed.

Other types of flexible foam can also be used, such as, for example, polypropylene foams, ionomer foams, polystyrene foams, polyvinylchloride foams, and silicone foams. These foams are only examples of types of foams which can be used and are not intended to limit the invention. Some of those foams mentioned are not heat sealable and only require an adhesive.

The preferred fastening means is detachable to allow replacement or washing. It is comprised of straps made of a laminate of foam sandwiched between a brushed Nylon material on one side and a smooth surface material on the other. One end of the strap as shown in the drawings contains a brushed Nylon material which interlocks with hooks on the palm side of the splint. The opposite end of the straps contains a hooked area which interlocks with the brushed Nylon material of the strap laminate, as shown in FIG. 9. Other types of fastening means can also be used, such as snaps, hooks, buckles and the like. However, the preferred straps provide cushioning as well as the securement of the splint on the hand. They are also capable of easy adjustments as might be required in the event of swelling.

PROCESS FOR MAKING THE ULNAR DEVIATION SPLINT OF THE INVENTION

The first step in making the ulnar deviation splint of the invention is comprised of first bending wire of the desired size and strength to provide a support frame which is proportional to fit and contact at least a portion of the palm of the hand to be treated.

Preferably the support frame is bent to a generally oblong shape as shown in FIG. 6 wherein the lower or base bar 16 is smaller than the top bar 18. The support frame 14 contains an ulnar side 22 and a radial side 20 which interconnect with the top bar 18 and base bar 16.

Figure 4:
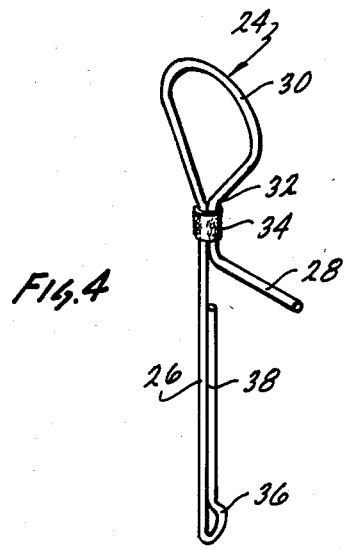
FIG. 4 shows the basic wire form of a flat generally rounded finger separator forming a part of the splint.
Figure 5:
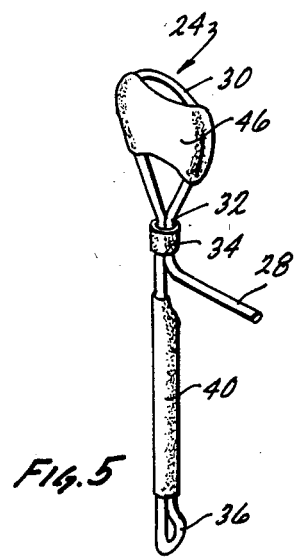
FIG. 5 shows the member of FIG. 4 with shrink fit plastic and a plastic sleeve enclosing portions thereof.

Next a wire is bent into the conformation shown in FIGS. 4 and 5 into the finger separators 24. The finger separators 24 are each comprised of a substantially round flat head member 30 having a neck 32 surrounded by a Nylon sleeve 34 from which extends a first extension 26 having a loop 36 and a second arm extension 28.

Shrink fit plastic tubing is implaced such that a portion 46 substantially covers each flat rounded member 30 and another portion 40 surrounds the leg extension 26. Heat is applied such as with a heat gun to shrink the plastic.

Upon completion of the finger separators 24, sections of shrink fit plastic tubing and sections of polytetrafluoroetheylene plastic or Nylon plastic tubing are threaded onto the frame member 18. The finger separators are then threaded through their loop 36 onto base bar 16 of frame 14.

Each of the arms 28 are bent and threaded into a separate plastic sleeve 42 which is partially covered with shrink fit plastic tubing 44 as shown in FIG. 7. The overlapping ends of the frame 14 at the ulnar side 22 are then soldered together and the sharp areas and frame angles are covered with shrink fit plastic tubing.

Upon completion of this step all of the shrink fit plastic is made to shrink by exposure to heat such as with a heat gun.

An overlapping piece of plastic foam 50 is secured to and extended partially over the leg extension 26. It is adhered to the base bar 16 of the base portion 14 and covers loops 36 of the finger separators 24. An additional piece of plastic foam 52 is adhered the palmar side of the splint along the top bar 18.

A sandwich is then made by placing the frame as shown in FIG. 7 between sheets of preferably polyethylene foam 54. The resulting sandwich is then heated as in an oven until the surface begins to melt. This condition is followed almost immediately by cutting the foam with a laminating die while the surfaces are still hot. This provides a good seal around the frame and finger support members.

While still hot, two slits for the straps are then cut into the resulting laminated foam sandwich. A first slit 56 and a second slit 58 are cut as shown in FIG. 8. If desired, a section of split plastic tubing 60 can then be inserted within the slit 58. The splint then looks substantially like that shown in FIG. 8. A piece of adhesive can be implaced between the splint and tubing 60 if desired to anchor it in place.

In order to shape the splint to the proportions of the hand, it is necessary to bend the ulnar side 21 upwardly towards the dorsal or back of the splint substantially even with the neck 32 of one of the finger separators 24. At the radial side 23 approximately one third from the frame base, a bend is made at approximately a seventy-five degree angle to allow for free movement of the thumb during use. This bend can be seen at 64 in FIGS. 3 and 10.

Each flat rounded member 30 of finger separators 24 is then rotated as shown in FIG. 9 around its axis approximately ninety degrees such that an imaginary plane containing top bar 18 of the frame 14 lies approximately at a ninety degree angle to an imaginary plane containing each separate finger separator head 30.

A hooked area 66 is then adhered to the palmar side of the splint as shown in FIG. 10, and straps 70 and 72 are threaded through the splint. Thus, one end of the strap 68 having the brushed material thereon is adhered to the hooked area 66. The free ends of the straps 70 and 72 are threaded up through slot 56 across the back or dorsum of the splint down through slot 58. The straps extend around sleeve 60 and radial side 23 of the splint. Here each strap is attached to itself through the hooked area 74 adhered to each end as seen in FIGS. 9 and 10.

If desired, an additional layer of abrasion resistant material such as vinyl or leather can be adhered to the cushioning material at the time of sealing and cutting of the splint conformation substantially as shown in FIG. 8.

Various other modifications of the invention are contemplated which would be obvious to those skilled in the art. These modifications can be resorted to without departing from the spirit and scope of the invention as defined by the following claims.

I claim:

1. An ulnar deviation splint comprising:
   a bendable wire support frame engagable with at least a portion of the palm of a hand to be treated and a plurality of bendable wire finger separation members which are comprised of substantially flat rounded members;
   fastening means for holding said splint against said palm; and,
   cushioning material enclosing at least part of said splint.

2. An ulnar deviation splint as claimed in claim 1 wherein:
   said support frame is bent to cup the ulnar side of the hand and is bent to fit the curve of the palm at the edge of the thumb.

3. An ulnar deviation splint as claimed in claim 1 further comprising:
   material extending at least partially within each of said rounded members.

4. An ulnar deviation splint as claimed in claim 3 wherein:
   said material is comprised of a plastic sheet.

5. An ulnar deviation splint as claimed in claim 4 wherein:
   said fastening means is detachable and is comprised of strap means.

6. An ulnar deviation splint as claimed in claim 5 wherein:
   said cushioning material is plastic foam and said strap means comprises at least one strap attached to said frame which can be secured to itself by means of interlocking hooks and brushed material each located on a portion of said strap.

7. An ulnar deviation splint comprising:
   a wire frame having a generally oblong shape proportioned to fit the palmar arch of the hand and having an ulnar side and a radial side, said ulnar side being bent to cup the ulnar side of the hand, said radial side being bent to accommodate the curve of the palm at the edge of the thumb;
   a plurality of wire finger separating members attached to said frame to separate the fingers during use and provide lateral resistance to ulnar drift;
   cushioning material enclosing at least a portion of said splint; and,
   detachable fastening means for said splint to secure said splint against the palm of a hand.

8. An ulnar deviation splint as claimed in claim 7 wherein:
   said finger separators comprise generally flat rounded members and include at least one extension by which they are attached to said frame.

9. An ulnar deviation splint as claimed in claim 8 wherein:
   said finger separators include material extending at least partially within said rounded members.

10. An ulnar deviation splint as claimed in claim 9 wherein:
    said material is shrink fit plastic.

11. An ulnar deviation splint as claimed in claim 7 wherein:
    said cushioning material is comprised of at least one layer of foamed plastic sheeting.

12. An ulnar deviation splint as claimed in claim 11 further comprising:
    a layer of abrasion resistant material overlying at least a portion of said cushioning material.

13. An ulnar deviation splint as claimed in claim 10 further comprising:
    shrink fit plastic covering any angles and sharp edges of said wire on said frame and finger separation members.

14. An ulnar deviation splint as claimed in claim 7 wherein:
    said detachable fastening means comprises at least one cushioning strap attached at one end to said splint and attachable to itself by means of a patch of hooks and interlocking with brushed material on said strap.

15. An ulnar deviation splint as claimed in claim 14 wherein:

said strap means includes two straps which extend over the back of the hand, one strap extending proximally to the metacarpophalangeal joint and the other strap extending distally to the metacarpophalangeal joint.

16. An ulnar deviation splint as claimed in claim 8 wherein:

said extension includes a loop at its end and further comprising a second separate extension from said rounded member, said rounded member having a neck area from which said extension initiates and which is surrounded by a plastic collar, said finger separator being attached to said support frame by one portion of said frame passing through said loop and a second portion of said frame being secured to said second extension by means of a surrounding sleeve.

17. A process for making an ulnar deviation splint comprising:

bending wire to provide a support frame to a generally oblong shape proportional to fit and contact at least a portion of the palmar arch of the hand and having an ulnar side and a radial side;

bending said ulnar side to cup the ulnar side of the hand;

bending said radial side to accommodate the curve of the palm at the edge of the thumb;

bending wire to provide a plurality of finger separators to provide a generally flat rounded member to separate the fingers during use and to provide lateral resistance to ulnar drift;

bending a first extension of said rounded member to form a loop at its end;

bending a second extension of said rounded member at an angle thereto;

attaching said finger separator to said support frame at said first and second extensions of said rounded members;

enclosing at least a portion of said splint with cushioning material; and, attaching fastening means to said splint to hold said splint against said palm.

18. A process as claimed in claim 17 further comprising:

covering at least a portion of said flat rounded member of said finger separator with a plastic material.

19. A process as claimed in claim 18 further comprising:

covering any angles and sharp edges of said wire on said frame and finger separation members with a plastic material.

* * * * *